(12) United States Patent
Szabo et al.

(10) Patent No.: US 9,395,348 B2
(45) Date of Patent: Jul. 19, 2016

(54) SYSTEM AND METHOD OF QUANTIFYING AN ORGANIC MATERIAL IN A SAMPLE

(71) Applicant: Schlumberger Technology Corporation, Sugar Land, TX (US)

(72) Inventors: Geza Horvath Szabo, Sugar Land, TX (US); Huang Zeng, Edmonton (CA); Ahmad Billal Sultani, Edmonton (CA)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 147 days.

(21) Appl. No.: 14/351,863

(22) PCT Filed: Oct. 22, 2012

(86) PCT No.: PCT/US2012/061250
§ 371 (c)(1),
(2) Date: Apr. 14, 2014

(87) PCT Pub. No.: WO2013/062879
PCT Pub. Date: May 2, 2013

(65) Prior Publication Data
US 2015/0001384 A1    Jan. 1, 2015

Related U.S. Application Data

(60) Provisional application No. 61/550,831, filed on Oct. 24, 2011.

(51) Int. Cl.
*G01V 5/00*    (2006.01)
*G01N 33/24*    (2006.01)
(Continued)

(52) U.S. Cl.
CPC ............ *G01N 33/241* (2013.01); *E21B 49/088* (2013.01); *G01N 21/01* (2013.01); *G01N 21/25* (2013.01); *G01N 33/28* (2013.01); *G01N 33/2823* (2013.01); *G01V 8/10* (2013.01); *G01N 2021/8405* (2013.01); *G01N 2201/068* (2013.01)

(58) Field of Classification Search
CPC . G01N 33/241; G01N 33/28; G01N 33/2823; G01N 21/01; G01N 21/25; G01N 2201/068; G01N 2021/8405; G01V 8/10; E21B 49/088
USPC .................................................. 250/253, 256
See application file for complete search history.

(56) References Cited

U.S. PATENT DOCUMENTS 3,994,342 A * 11/1976 Healy ..................... C09K 8/584
166/270.1
4,271,907 A * 6/1981 Gale ....................... C09K 8/584
166/270.1
(Continued)

FOREIGN PATENT DOCUMENTS

EP    0543057    5/1993
WO    2011/135466    11/2011

OTHER PUBLICATIONS

S. Davies, et al, "Quantification of oil and water in preserved reservoir rock by NMR spectroscopy and imaging," Magnetic Resonance Imaging, 1994, vol. 12, No. 2, pp. 349-353.
(Continued)

*Primary Examiner* — David Porta
*Assistant Examiner* — Gisselle Gutierrez
(74) *Attorney, Agent, or Firm* — Bridget M. Laffey (57) ABSTRACT

A system and methodology enables improved quantification of an organic material, e.g. oil, in a sample. The technique comprises adding a substance to a two-phase sample containing the organic material and water. The substance is mixed through the sample until the constituents of the sample are solubilized to create an optically clear mixture. An optical technique is employed with respect to the optically clear mixture to quantitatively analyze the organic material in the sample.

14 Claims, 9 Drawing Sheets

(51) Int. Cl.
   *G01N 21/25* (2006.01)
   *G01N 21/01* (2006.01)
   *G01N 33/28* (2006.01)
   *E21B 49/08* (2006.01)
   *G01V 8/10* (2006.01)
   *G01N 21/84* (2006.01)

(56) References Cited

U.S. PATENT DOCUMENTS 4,980,295 A    12/1990    Udy
6,809,819 B1   10/2004    Vinjamoori et al.
2010/0115714 A1   5/2010   Cassway et al.

OTHER PUBLICATIONS

M.A. Lopez-Quintela, et al, "Microemulsion dynamics and reactions in microemulsions," Current Opinion in Colloid and Interface Science 9 (3-4), 2004, pp. 264-278.

Y.V. Griko, "Energetics of Ca2+-EDTA interactions: Calorimetric study," Biophysical Chemistry 79 (2), 1999, pp. 117-127.

A.N. Patel, "Ternary phase equilibrium studies of the systems tetrahydrofuran—water-solvents," Journal of Chemical Technology and Biotechnology, vol. 33, Issue 5, pp. 245-248, Jul. 1983.

* cited by examiner

| Time (min) | 1% EDTA-4Na (vol %) | Brine (vol %) | 10% AOT in IPA (vol %) | Total flow (ml/min) |
|---|---|---|---|---|
| 0-15 | 25 | 25 | 50 | 3.0 |
| 15.1-25 | 20 | 30 | 50 | 3.0 |
| 25.1-35 | 15 | 35 | 50 | 3.0 |
| 35.1-45 | 10 | 40 | 50 | 3.0 |

| Time (min) | 1% EDTA-4Na (vol %) | Brine (vol %) | 10% AOT in IPA (vol %) | Total flow (ml/min) |
|---|---|---|---|---|
| 0-15 | 20 | 20 | 60 | 3.0 |
| 15.1-25 | 16 | 24 | 60 | 3.0 |
| 25.1-35 | 12 | 28 | 60 | 3.0 |
| 35.1-45 | 8 | 32 | 60 | 3.0 |

| Time (min) | 1% EDTA-4Na (vol %) | Brine (vol %) | 10% AOT in IPA (vol %) | Total flow (ml/min) |
|---|---|---|---|---|
| 0-15 | 15 | 15 | 70 | 3.0 |
| 15.1-25 | 12 | 18 | 70 | 3.0 |
| 25.1-35 | 9 | 21 | 70 | 3.0 |
| 35.1-45 | 6 | 24 | 70 | 3.0 |

| Time (min) | 1% EDTA-4Na (vol %) | Brine (vol %) | 10% AOT in IPA (vol %) | Total flow (ml/min) |
|---|---|---|---|---|
| 0-15 | 10 | 10 | 80 | 3.0 |
| 15.1-25 | 8 | 12 | 80 | 3.0 |
| 25.1-35 | 6 | 14 | 80 | 3.0 |
| 35.1-45 | 4 | 16 | 80 | 3.0 |

| Time (min) | Toluene (vol %) | Brine (vol %) | Pseudo-solution (vol %) | Total flow (ml/min) |
|---|---|---|---|---|
| 0-20 | 14 | 11 | 75 | 3.0 |
| 20.1-40 | 16 | 9 | 75 | 3.0 |
| 40.1-60 | 18 | 7 | 75 | 3.0 |

FIG. 15

SYSTEM AND METHOD OF QUANTIFYING AN ORGANIC MATERIAL IN A SAMPLE

BACKGROUND

Analyzing hydrocarbon fluid samples can provide insight with respect to characteristics of hydrocarbons in a hydrocarbon fluid reservoir. For example, analysis of fluid from a core sample, particle pack, or other formation rock sample can provide data on a given hydrocarbon fluid reservoir. The analysis may be helpful in evaluating oil content, potential production, and the economic value of fluids produced from the hydrocarbon fluid reservoir.

SUMMARY

In general, the present disclosure provides for a system and method of quantifying an organic material, e.g. oil, in a sample. The technique comprises adding a substance to a sample containing the organic material and water. The substance is mixed through the sample until the oil (or other organic material) and water of the sample are solubilized to create an optically clear mixture. An optical technique is employed with respect to the optically clear mixture to quantitatively analyze the oil (or other organic material) in the sample.

However, many modifications are possible without materially departing from the teachings of this disclosure. Accordingly, such modifications are intended to be included within the scope of this disclosure as defined in the claims.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein, and.

DETAILED DESCRIPTION

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

The present disclosure generally relates to a system and methodology for quantifying organic material, e.g. oil, in a sample. According to an embodiment, the technique comprises adding a substance to a sample containing oil and water. Depending on the application, the oil and water sample may be obtained from a variety of sources, including various mixtures of oil and water retrieved from subterranean operations, e.g. production operations and/or injection operations. The oil and water sample may also be obtained during retrieval methods applied to formation rock samples. For example, a brine mixture may be used to retrieve a hydrocarbon fluid, e.g. oil, from a core sample, particle pack, or other formation rock sample from a given reservoir. In a variety of these applications, the substance is mixed through the sample until, for example, the oil, water and salt of the sample are solubilized to create an optically clear mixture. An optical technique is employed with respect to the optically clear mixture to quantitatively analyze the oil in the sample. For example, a detection and analysis system may employ a spectrophotometer to quantify oil in the sample.

By way of example, the system and methodology may be used for the quantitative determination of the amount of recovered oil phase from a rock sample. In such an embodiment, the detection and analysis system may utilize a co-injected mixture which is altered to simultaneously solubilize recovered oil, water, and salt. According to an example, a substance in the form of a fluid mixture is co-injected with an oil and brine, two-phase stream from a core sample to form an optically clear, single-phase fluid. The substance may then be thoroughly mixed with the two-phase oil and brine sample in a dynamic mixer and used for oil concentration determination via a spectrophotometer.

It should be noted that certain fluid mixtures, such as crude oil and water, produce a multiphase system when mixed. Such a multiphase system can cause strong light scattering when ultraviolet-visible spectroscopy is employed to determine, for example, crude oil concentration. The emulsified oil or water droplets in the multiphase system divert part of the incident light beam in the spectroscopic cell, and the diverted fraction of light may not reach the spectroscopic detector. As a result, the apparent optical density is considerably increased in such multiphase fluids. Consequently, testing of such fluids can result in a misleading concentration determination.

In some applications, the techniques described herein may be utilized in a laboratory characterization technique used to study reservoir rock samples for enhanced oil recovery. In such an application, a high-performance liquid chromatography system may be employed with an optical detector, such as a spectrophotometer. An example of a spectrophotometer includes a UV-visible spectrophotometric detector. The high performance liquid chromatography system, along with its spectrophotometer, may be used to analyze complex mixtures and to determine quantitatively the amount of organic phase, e.g. oil, released from a core or particle pack.

Figure 1:
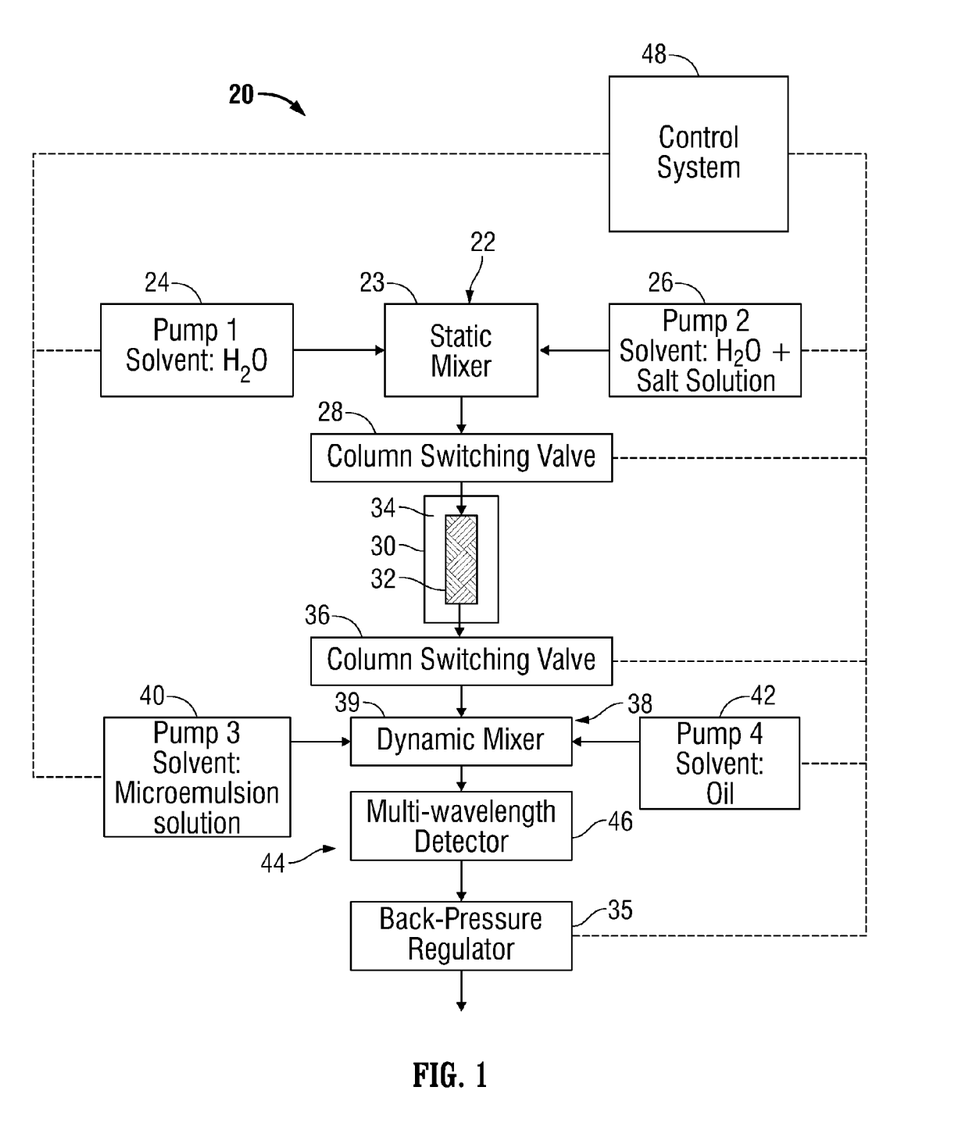
FIG. 1 is a schematic illustration of an example of a system for testing a sample containing an organic substance, e.g. oil, according to an embodiment of the disclosure.

Referring generally to FIG. 1, an embodiment of a quantification system is illustrated. By way of example, the quantification system may comprise a detection and analysis system employed to test for the amount of an organic phase, e.g. oil, in a fluid sample. The fluid sample may be obtained from a variety of locations and environments, including downhole environments. However, the fluid sample may also be obtained in a laboratory setting by, for example, utilizing a brine mixture to release oil from a core, particle pack, or other formation rock sample.

In the example illustrated in FIG. 1, a quantification system 20 comprises a variety of features for quantifying a hydrocarbon, e.g. oil, in a fluid sample. In this particular embodiment, the fluid sample is obtained from a formation rock sample by releasing oil from the formation rock sample with a brine composition. As illustrated, quantification system 20 comprises a mixing system 22, including a mixer 23 (e.g. a static mixer) fed by a pump or a plurality of pumps 24, 26. By way of example, a pair of pumps 24, 26 may be used to deliver water and water plus salt solution, respectively, to the mixer 23 to establish a brine composition for recovery of a hydrocarbon, e.g. oil. The brine composition may be selectively delivered, via a column switching valve 28, to a column 30 designed to hold a formation rock sample 32, such as a core sample. By way of example, the column 30 may be packed with oil-wet calcite particles. Additionally, the column 30 may comprise an oven 34 which operates in cooperation with a back-pressure regulator 35 to simulate reservoir conditions, e.g. conditions with temperatures up to 200° C. (392° F.) and pressures up to 10 MPa (1450 psi).

In the embodiment illustrated, the brine composition releases oil from the rock sample 32 to form a fluid sample which exits column 30 via an outlet end coupled with column switching valve 36. Depending on how much oil is released within the column 30, the fluid sample can be a complex mixture of oil, water, and salt which is then mixed into an optically clear liquid for quantification. For example, the fluid sample may be delivered into a mixing system 38, including a mixer 39 (e.g. a dynamic mixer). A substance is introduced into the mixer 39 to solubilize the oil, water, and salt in the fluid sample to create an optically clear, single-phase fluid. The substance, e.g. a micro-emulsion solution, may be fed to the dynamic mixer 39 by a pump or by a plurality of pumps 40, 42. In the particular example illustrated, pump 40 delivers the micro-emulsion solution to the mixer 39, and pump 42 delivers another additive (e.g. oil which may be in the form of a toluene or a toluene-heptane mixture in, for example, a 1:1 volume ratio at ambient temperature) to the mixer 39 for thorough mixing. As described in greater detail below, the substance may comprise a variety of pseudo-solutions and/or other materials designed to dissolve or otherwise solubilize the oil, water, and salt of the sampled fluid into a clear, single-phase liquid for quantification. In some applications, a dye, e.g. Oil Blue N, may be added to the mixture because a characteristic peak of the dye can be observed at a visible wavelength and this observation can be used to facilitate oil quantification.

By way of example, the mixer 39 may utilize a magnetic stir bar or other mixing features to mix the substance, e.g. solvent, with the sampled fluid containing oil and brine. The mixing solubilizes the fluid sample to form an optically clear liquid which is passed to a detection and analysis system 44 that employs optical techniques to determine the quantity of oil in the oil, water, and salt sample. By way of example, the detection and analysis system 44 may comprise a multi-wavelength detector such as a spectrophotometer 46 which can be used to determine the oil quantity in the clear liquid as it passes through the detector.

The quantification system 20 also comprises a control system 48 which controls the operation of the mixing system 22, column 30, mixing system 38, pumps, and other components of the quantification system 20. By way of example, control system 48 may be a processor-based control system, such as a computer control system. The computer control system 48 may utilize various types of software to enable adaptable programming, thus enabling control over the operation of quantitation system 20 according to predetermined parameters. The control system 48 also works in cooperation with the spectrophotometer 46 to analyze oil (or other organic material) content in the fluid sample and thus in the formation rock sample 32.

The various components of quantification system 20 may be used in a variety of forms and arrangements. By way of specific examples, the pumps 24, 26, 40 and 42 may be selected from a variety of pumps available from JASCO, Inc. of Easton, Md., USA. The column 30 may be selected from various columns available from Isolation Technologies of Middleboro, Mass., USA; and an example suitable for some applications is a column approximately 150 mm long with an inside diameter of 4.6 mm. The mixers 23, 39, the column switching valves 28, 36, and the back-pressure regulator 35 may also be selected from various components available from JASCO, Inc. The control system 48 may comprise a variety of processor-based systems, such as PC-based computer systems, which interact with the other system components through a computer interface, such as a suitable computer interface available from JASCO, Inc. The spectrophotometer 46 may be a UV-visible spectrophotometer, such as the MD-2015 Plus Multiwavelength Detector available from JASCO, Inc. These are just a few examples of suitable components that may be used to construct the quantification system 20, however, a variety of other types of components, systems, and arrangements may be used for quantifying oil or other organic materials in the fluid sample.

Figure 2:
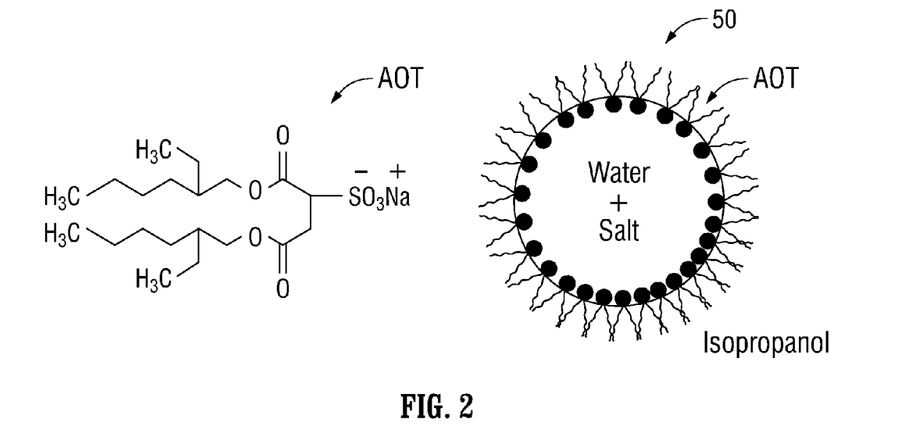
FIG. 2 is a schematic representation of a water-in-oil microemulsion that may be used in the system illustrated in FIG. 1, according to an embodiment of the disclosure.

Referring generally to FIG. 2, a graphical representation is provided of constituents of a substance 50 that may be added to the fluid sample to create the optically clear, single-phase fluid for analysis by spectrophotometer 46. However, substance 50 may comprise additional and/or other constituents in a variety of ratios as discussed in greater detail below. In this example, the substance 50 comprises sodium bis(2-ethylhexyl)sulfosuccinate (AOT), and FIG. 2 illustrates the structure of AOT. AOT is an anionic surfactant, which can stabilize water-in-oil microemulsions. In the example of FIG. 2, a graphical representation is provided of the AOT structure and its arrangement in a water-in-oil micro-emulsion. (The AOT structure is described in "Microemulsion dynamics and reactions in microemulsions"—López-Quintela, M. A., Tojo, C., Blanco, M. C., García Rio, L., Leis, J. R. *Current Opinion in Colloid and Interface Science* 9 (3-4), pp. 264-278—2004.) Therefore, this substance may be used to produce a water phase within the micelle, which can dissolve salts, and an organic phase (the medium), which can dissolve oil.

Figure 3:
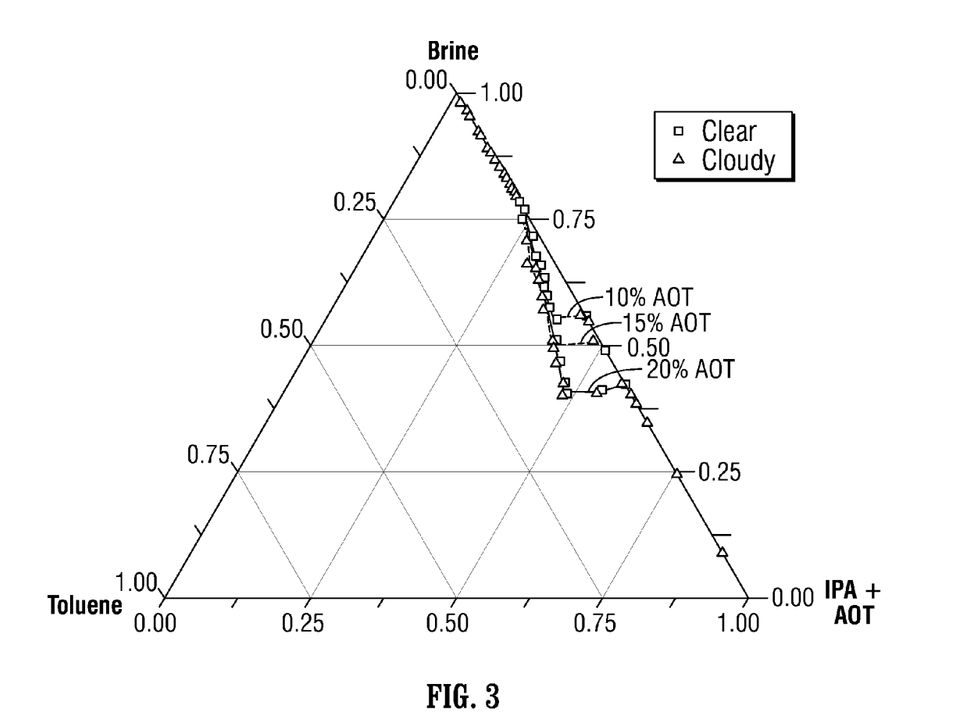
FIG. 3 is a ternary phase diagram of brine, toluene and isopropanol (IPA) plus sodium bis(2-ethylhexyl)sulfosuccinate (AOT), according to an embodiment of the disclosure.

In some applications, the substance 50 may comprise AOT mixed in isopropanol (IPA). Referring generally to FIG. 3, a graphical representation is provided which shows the results of varying the amount of AOT in IPA on the single-phase range boundary between brine, toluene and IPA+AOT. In this example, the brine solution was synthetic seawater, containing 0.013 M $CaCl_2$, 0.024 M $Na_2SO_4$, 0.045 M $MgCl_2$ and 0.45 M NaCl. The concentration of AOT in isopropanol varied between 10%, 15% and 20% by mass. In the graphical representation, the observed clear mixtures are represented as squares, and the non-clear (cloudy) mixtures are represented as triangles. It can be seen that the boundary of the single-phase range expands with increasing amounts of AOT. For example, with 10% AOT in IPA, the single-phase region is between 18% and 38% IPA+AOT. It is also capable of dissolving up to 6% toluene by mass. If the AOT is increased to 20%, the single-phase region expands between 19% and 57% IPA+AOT. It is capable of dissolving more toluene, e.g. up to 11% by mass. The result is that increasing the amount of AOT in isopropanol, expands the single-phase region, and allows for more toluene to be dissolved.

The substance 50 may also comprise ethylenediaminetetraacetic acid (EDTA) which may be mixed with water or another suitable material. With respect to EDTA, a reaction mechanism for $Ca^{2+}$ binding to EDTA involves displacement of a proton on the nitrogen site. In this example, to improve the single-phase range boundary, water and EDTA can be added to the IPA+AOT mixture. EDTA binds to calcium or magnesium ions to prevent salt precipitation. The acid dissociation constants (pKa) for the carboxyl groups are 1.15, 1.15, 2.12 and 2.57 and the pKa for the amino groups are 6.16 and 10.26. At a pH of approximately 7, one amino group is protonated, so the binding of calcium is associated with the release of a single proton. The suggested mechanism is that the calcium interacts with the two carboxyl groups close to the nitrogen atom with the available lone pair of electrons. Then this lone pair of electrons can form the third coordinated bond with calcium. After the three bonds have formed, the other nitrogen atom can release its proton more favorably. This results in a stepwise formation of the last coordinated bonds. (See "Energetics of Ca2+-EDTA interactions: calorimetric study"—Griko, Y. V., *Biophysical Chemistry* 79 (2), pp. 117-127-1999.)

Figure 4:
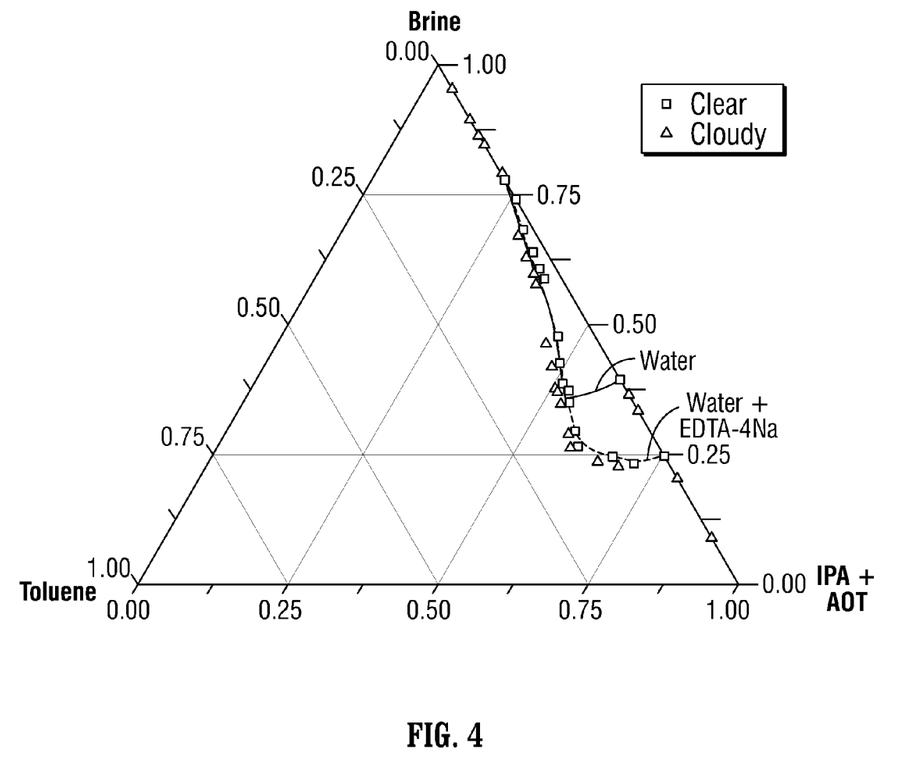
FIG. 4 is a ternary phase diagram of brine, toluene and water or 1% ethylenediaminetetraacetic acid-sodium salt (EDTA-4Na) in water in a 16% AOT in isopropanol (IPA) solution, according to an embodiment of the disclosure.

For some applications, substance 50 may comprise a mixture of water, EDTA, IPA, and AOT. In FIG. 4, for example, a graphical representation is provided which shows the effect of adding water and EDTA in an IPA+AOT mixture on the single-phase range boundary with brine and toluene. The observed clear mixtures are represented as squares, and the non-clear mixtures are represented as triangles. The form of EDTA used can be the tetrasodium form. In this example, a 16% AOT in IPA solution was prepared. In a first example, water was added to IPA+AOT, in a 1:9 mass ratio. In a second example, 1% EDTA-4Na in water was added to IPA+AOT, in a 1:9 mass ratio. It can be seen that the single-phase range boundary expands with the addition of water and EDTA-4Na. With the addition of water, the single-phase region is between 20% and 61% IPA+AOT and it is capable of dissolving up to 11% toluene. Addition of EDTA-4Na expands the single-phase region to between 20% and 78% IPA+AOT and is capable of dissolving up to 14% toluene. The result is that the addition of water alone helps to expand the single-phase region and dissolve more toluene. The addition of water and EDTA-4Na helps to further expand the single-phase region and dissolves even more toluene.

Figure 5:
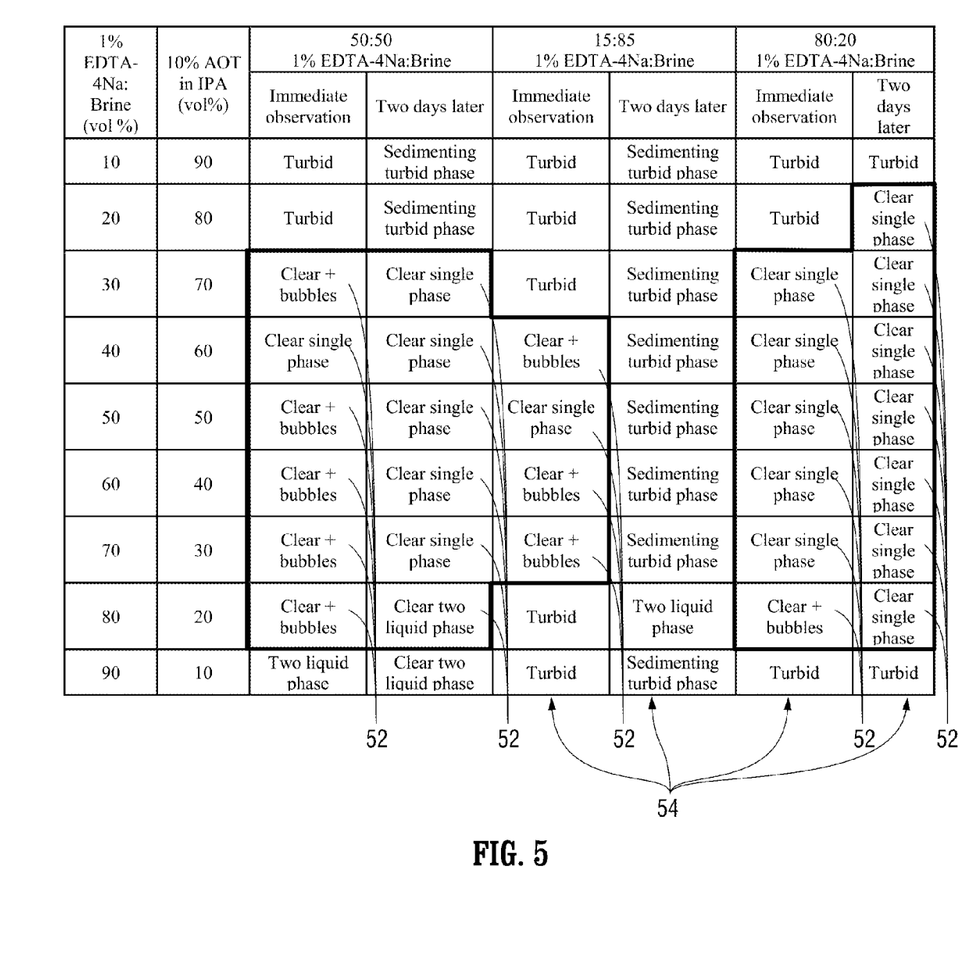
FIG. 5 is a tabular representation of phase behavior of various sample mixtures under static conditions, according to an embodiment of the disclosure.

Referring generally to FIG. 5, a table is provided to summarize observations of phase behavior for brine when substance 50 comprises IPA, AOT, water, and EDTA-4Na. In the specific examples provided, the table of FIG. 5 illustrates observations made of the IPA/AOT/water/EDTA-4Na mixture (pseudo-solution) with brine, where the cells 52 represent clear mixtures, and the remaining cells 54 represent non-clear mixtures. For purposes of this example, consider three separate solutions in which each one is mixed together in different proportions. A first is 1% EDTA-4Na in water, a second is 10% AOT in IPA, and a third is a synthetic seawater brine solution. The 1% EDTA-4Na solution was mixed with brine in three different mass ratios, 50:50, 15:85 and 80:20. A 10% AOT in IPA solution was then mixed in, and the mixture was observed and recorded immediately after mixing, and two days later. In the table, the 15:85 ratio of 1% EDTA-4Na with brine represents another mixture used for dynamic experiments and comparisons. As can be seen, the mixture appears to be clear immediately after mixing, however, two days later there is some sedimentation and a turbid phase is observed. This shows that there was instability with the mixture, and that increasing the amount of 1% EDTA-4Na solution resolves this issue.

Figure 6:
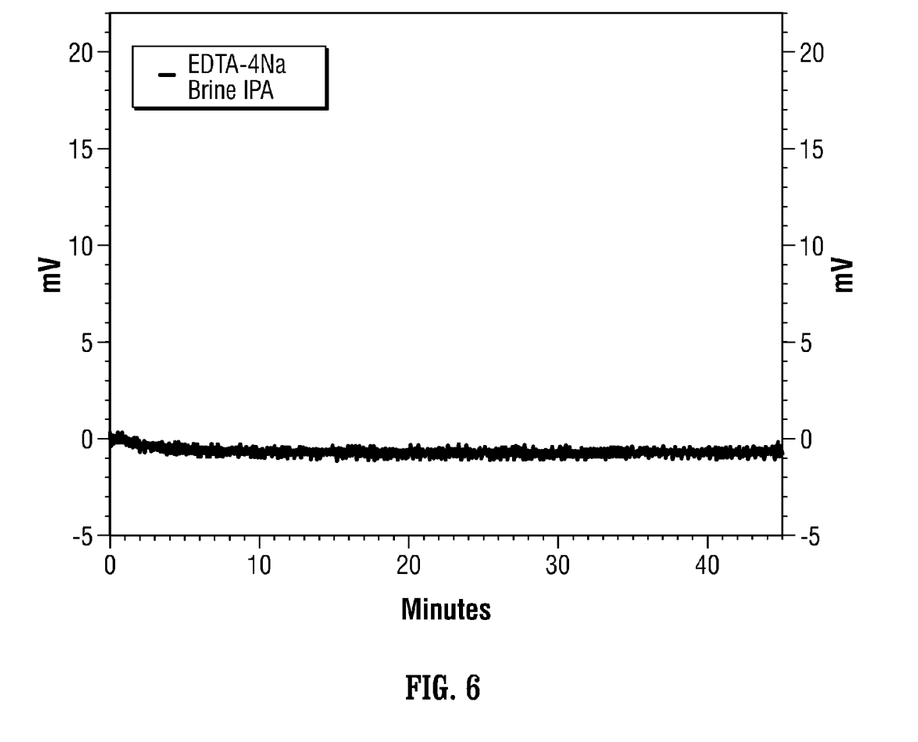
FIG. 6 is a diagrammatic representation showing stability of pseudo-solution with varying amounts of 1% EDTA-4Na and brine, according to an embodiment of the disclosure.
Figure 7:
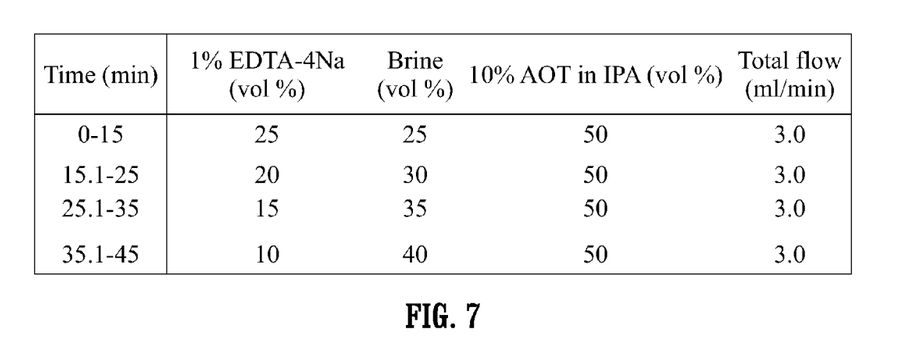
FIG. 7 is a tabular representation of the experimental flow conditions represented in FIG. 6, according to an embodiment of the disclosure.

Referring generally to FIG. 6, a graphical representation is provided which shows the results of varying the composition of the substance 50, e.g. pseudo-solution, in the presence of brine. FIG. 7 illustrates in tabular form the experimental flow conditions with respect to the example illustrated in FIG. 6. In this example, the quantification system 20 illustrated in FIG. 1 was reconfigured so that pump 24, pump 26, and pump 40 inject directly into the dynamic mixer 39. To maintain a consistent residence time in the dynamic mixer 39, the total flow was maintained at 3.0 ml/min. The flow of 10% AOT in IPA was held constant while decreasing the amount of 1% EDTA-4Na and increasing the amount of brine to maintain a constant flow. For the amount of brine tested, there was no interference in the system. In some applications it may be helpful, however, to increase the amount of IPA+AOT because the IPA is involved in dissolving the oil.

Figure 8:
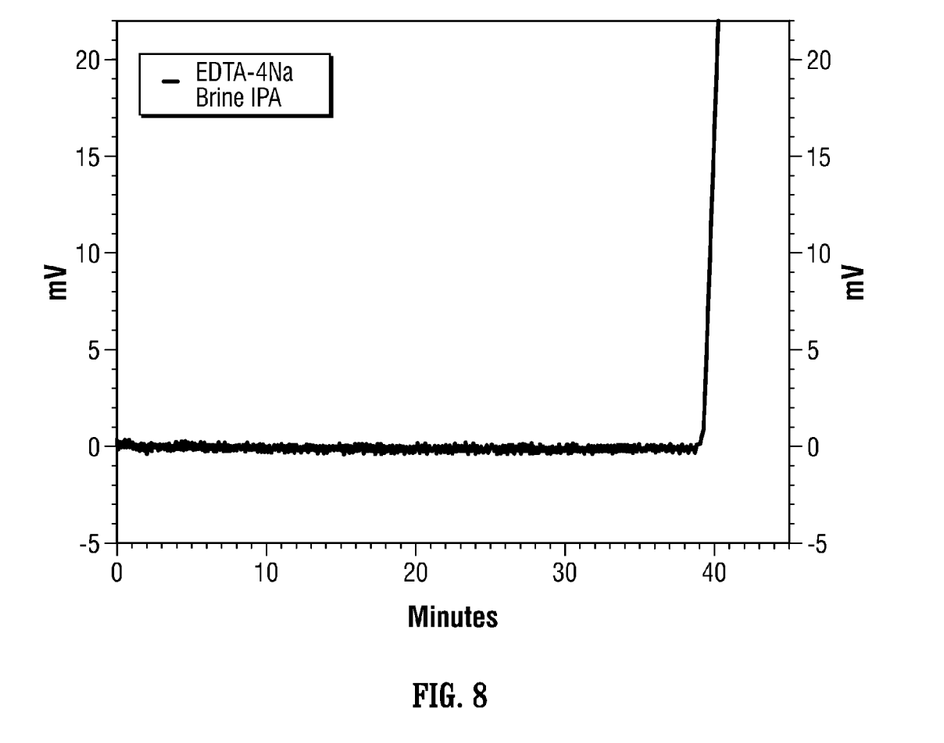
FIG. 8 is a diagrammatic representation showing stability of pseudo-solution with varying amounts of 1% EDTA-4Na and brine, according to an embodiment of the disclosure.
Figure 9:
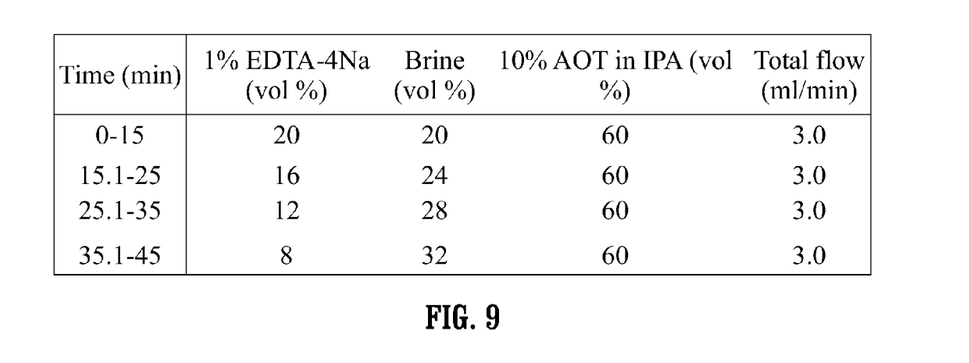
FIG. 9 is a tabular representation of the experimental flow conditions represented in FIG. 8, according to an embodiment of the disclosure.

Referring generally to FIG. 8, a graphical representation is provided which shows the stability of the pseudo-solution substance 50 with varying amounts of 1% EDTA-4Na and brine. FIG. 9 illustrates in tabular form the experimental flow conditions with respect to the example illustrated in FIG. 8. In this example, the graphical and tabular representations show the results of maintaining IPA+AOT at 60% of total system flow, while varying the amount of brine and 1% EDTA-4Na solution. In this particular example, the system is stable until the 1% EDTA-4Na solution is decreased to 8% and brine is increased to 32% of total flow.

Figure 10:
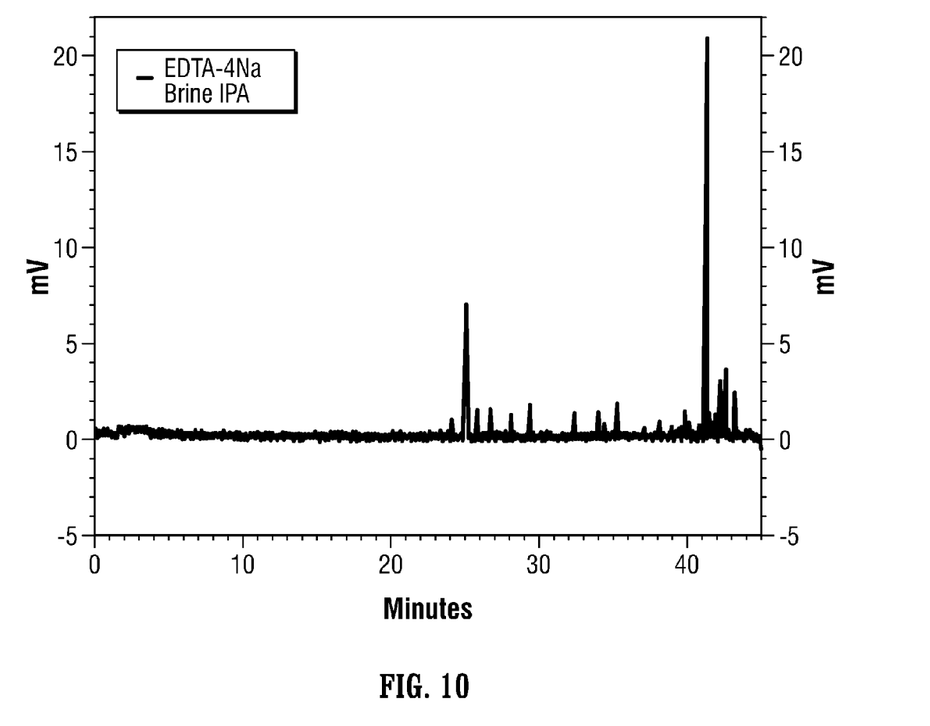
FIG. 10 is a diagrammatic representation showing stability of pseudo-solution with varying amounts of 1% EDTA-4Na and brine, according to an embodiment of the disclosure.
Figure 11:
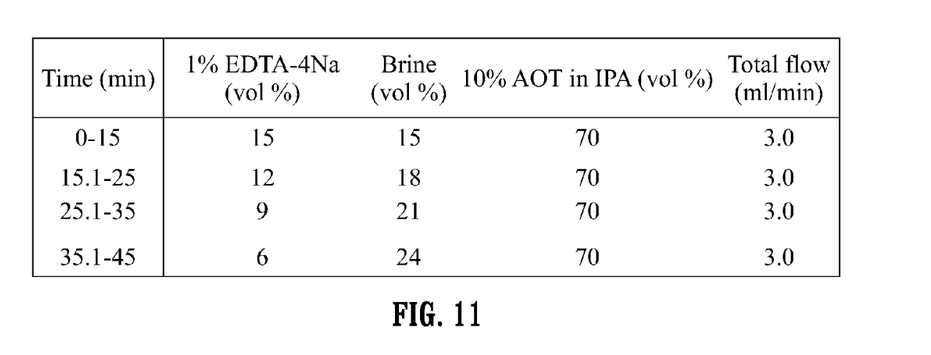
FIG. 11 is a tabular representation of the experimental flow conditions represented in FIG. 10, according to an embodiment of the disclosure.

Referring generally to FIG. 10, another graphical representation is provided which shows the stability of the pseudo-solution substance 50 with varying amounts of 1% EDTA-4Na and brine. FIG. 11 illustrates in tabular form the experimental flow conditions with respect to the example illustrated in FIG. 10. In this example, the graphical and tabular representations show the results of maintaining IPA+AOT at 70% of total system flow, while varying the amount of brine and 1% EDTA-4Na solution. In this example, the system is stable until the 1% EDTA-4Na solution is decreased to 12% and brine is increased to 18% of total flow.

Figure 12:
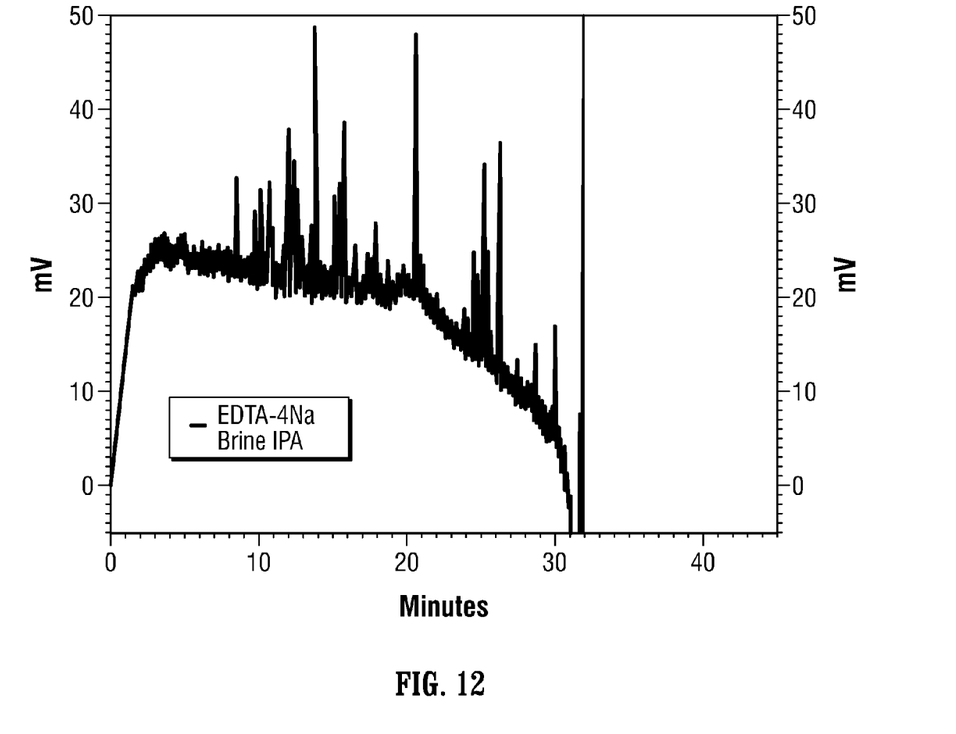
FIG. 12 is a diagrammatic representation showing stability of pseudo-solution with varying amounts of 1% EDTA-4Na and brine, according to an embodiment of the disclosure.
Figure 13:
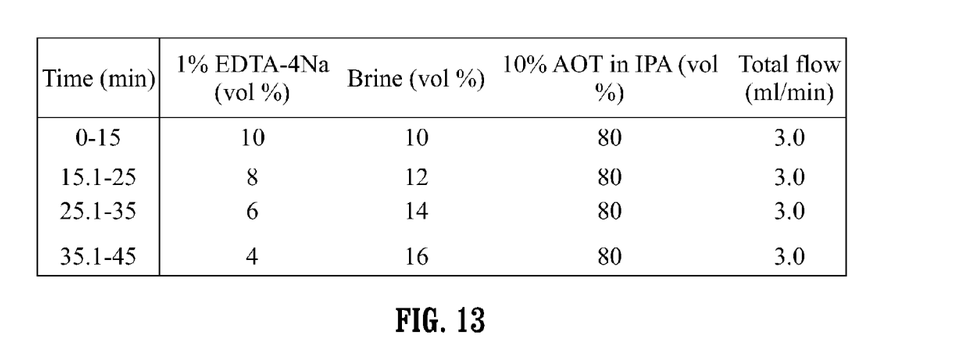
FIG. 13 is a tabular representation of the experimental flow conditions represented in FIG. 12, according to an embodiment of the disclosure.

Referring generally to FIG. 12, another graphical representation is provided which shows the stability of the pseudo-solution substance 50 with varying amounts of 1% EDTA-4Na and brine. FIG. 13 illustrates in tabular form the experimental flow conditions with respect to the example illustrated in FIG. 12. In this example, the graphical and tabular representations show the results of maintaining IPA+AOT at 80% of total system flow while varying the amount of brine and 1% EDTA-4Na solution. In this example, the system is not stable because a steady baseline is not obtained and the signal noise is much greater, almost +/−3 mV compared to +/−0.3 mV previously. Based on these experiments and observations, it was determined that one example of a suitable composition of the pseudo-solution substance 50 is 65% of the 10% AOT in IPA, and 35% of the 1% EDTA-4Na in water. In these examples, the runs made on the quantification system 20 may be performed using a total flow of 3.0 ml/min, of which 75% is the pseudo-solution and 25% is brine or toluene. The total flow depends on the characteristics of the dynamic mixer 39, including mixer size and residence time with mixing. By way of example, suitable parameters may comprise a flow of 3.0 ml/min with a 1.5 ml dynamic mixer.

Figure 14:
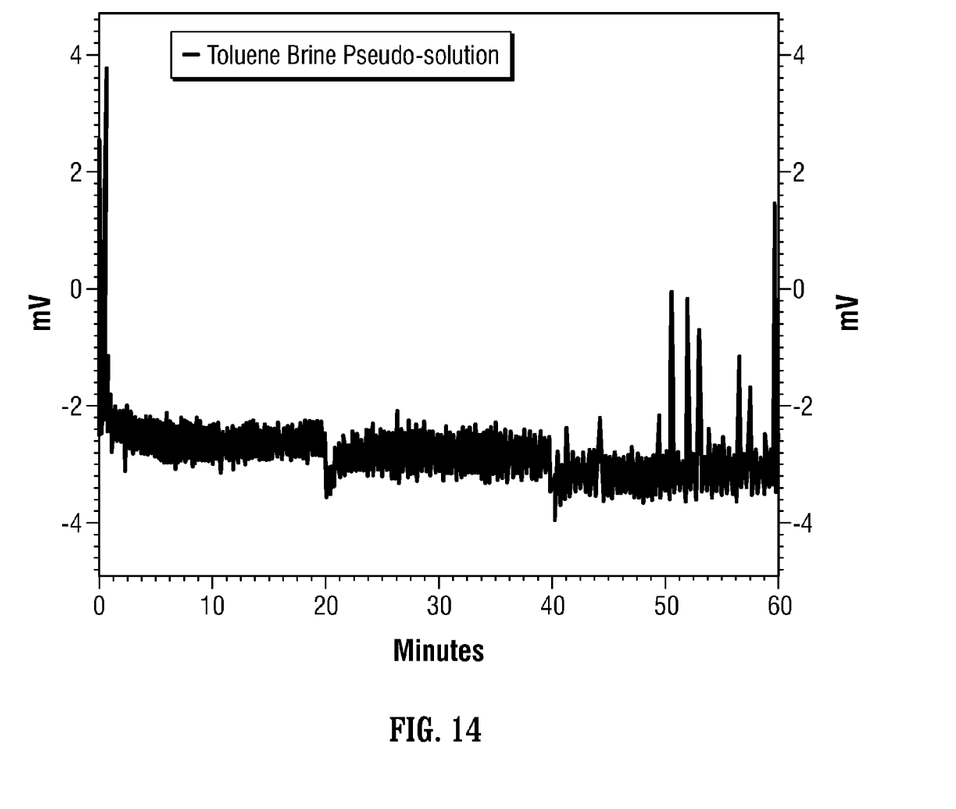
FIG. 14 is a diagrammatic representation showing a total flow of 3.0 ml per minute, of which 75% is pseudo-solution, with up to 18% toluene injected, and the remainder is brine solution, according to an embodiment of the disclosure.
Figure 15:
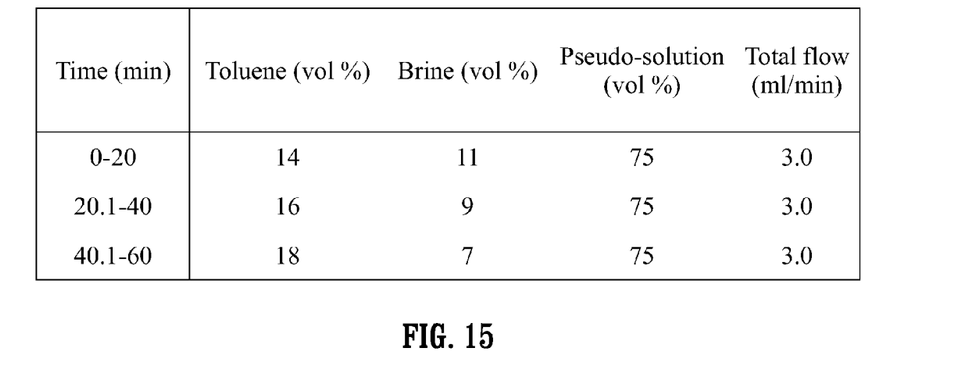
FIG. 15 is a tabular representation of the experimental flow conditions represented in FIG. 14, according to an embodiment of the disclosure.

Referring generally to FIG. 14, another graphical representation is provided which shows the pseudo-solution substance 50 at 75%, a total flow of 3.0 ml per minute, and with up to 18% toluene injected. FIG. 15 illustrates in tabular form the experimental flow conditions with respect to the example illustrated in FIG. 14. In this example, the graphical and tabular representations show results from an experiment where the total flow rate was held constant at 3.0 ml/min. Pseudo-solution substance 50 made up 75% of the total flow, and brine was decreased from 11% to 7%, while toluene was increased from 14% to 18%. As illustrated, results show the baseline is stable, except for the 18% toluene injection, where noise contained spikes as large as 5 mV. Based on these results, the quantification system 20 readily tolerates up to 16% toluene without any baseline disturbance.

In operational examples, various mixtures of substance 50 may be added to a sample containing, for example, oil, water, and salt in the quantification system 20. Thorough mixing of the substance 50 with the fluid sample solubilizes the multiphase oil, water, and salt sample to create a clear, single-phase fluid that may be subjected to optical analysis via, for example, spectrophotometer 46. Accordingly, various mixtures of the substance 50 may be used to quantify the model oils released from cores or particle packs. Using the quantification system 20, e.g. a high-performance liquid chromatography system, with its optical detector, e.g. a UV-visible spectrophotometer, experiments can be conducted quickly, quantitatively and cheaply to quantitatively assess oil content in a given sample. The development of a mixture to dissolve oil, water, and salt into one optically clear mixture enables proper operation of the spectrophotometer 46. With a mixture of IPA, AOT, water, and/or EDTA-4Na, interference in the spectrophotometer is substantially reduced or avoided. The system and methodology enable use of a micro-emulsion technique to overcome the detrimental effects of a two-phase sample by converting the sample into a clear, single-phase fluid.

Depending on the material and/or environment from which the oil or other organic material is obtained for quantitative analysis, the quantification system may be constructed in a variety of configurations with many types of components. For example, various columns or other chambers may be employed to remove the subject material, e.g. oil, from the rock sample or other sample containing the material. Additionally, a variety of pumps and mixing chambers may be employed to mix the brine solution which is combined with, for example, the oil to create the fluid sample for analysis. The substance added to the fluid sample to create a clear, single-phase fluid for analysis may be injected into the fluid sample or combined with the fluid sample according to other suitable techniques. The added substance and a fluid sample may be mixed by a variety of mixing features employed with a suitable mixing chamber. Additionally, the substance added to the fluid sample may be in fluid form or other suitable form and may comprise a variety of constituents in various ratios, as discussed above with respect to several different embodiments of the substance.

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

What is claimed is:

1. A method of quantifying oil in a sample, comprising:
   obtaining a fluid sample including oil from a reservoir;
   simultaneously solubilizing oil, water, and salt contained in the fluid sample to create an optically clear single-phase fluid, wherein simultaneously solubilizing oil, water, and salt contained in the fluid sample comprises injecting a substance into the fluid sample to create the optically clear single-phase fluid, and wherein the substance comprises a mixture of sodium bis(2-ethylhexyl)sulfosuccinate (AOT), isopropanol (IPA), water, and ethylenediaminetetraacetic acid-sodium salt (EDTA-4Na); and
   using a spectrophotometer to analyze the optically clear single-phase fluid so as to determine the concentration of oil in the fluid sample.

2. The method of claim 1, wherein obtaining the fluid sample comprises obtaining the oil from a core sample taken from the reservoir.

3. A method of quantifying oil in a sample, comprising:
   obtaining a fluid sample including oil from a reservoir;
   simultaneously solubilizing oil, water, and salt contained in the fluid sample to create an optically clear single-phase fluid, wherein simultaneously solubilizing oil, water, and salt contained in the fluid sample comprises injecting a substance into the fluid sample to create the optically clear single-phase fluid, wherein the substance comprises a mixture of approximately 10% sodium bis(2-ethylhexyl)sulfosuccinate (AOT) in isopropanol (IPA); and
   using a spectrophotometer to analyze the optically clear single-phase fluid so as to determine the concentration of oil in the fluid sample.

4. The method of claim 3, wherein injecting the substance into the fluid sample comprises injecting a second mixture of approximately 1% ethylenediaminetetraacetic acid-sodium salt (EDTA-4Na) in water.

5. The method of claim 4, wherein injecting the substance into the fluid sample comprises combining the mixture of approximately 10% AOT in IPA with the second mixture of approximately 1% EDTA-4Na in water at a ratio of approximately 65% to 35%.

6. The method of claim 1, wherein using a spectrophotometer to analyze the optically clear single phase fluid comprises using the spectrophotometer as part of a high performance liquid chromatography system.

7. A method of quantifying oil in a sample, comprising:
   adding a substance to a sample containing oil and water, wherein adding the substance comprises injecting a mixture of sodium bis(2-ethylhexyl)sulfosuccinate (AOT), isopropanol (IPA), water, and ethylenediaminetetraacetic acid-sodium salt (EDTA-4Na);

mixing the substance through the sample until the oil and water of the sample are dissolved to create an optically clear mixture; and using an optical technique to determine the quantity of oil in the sample.

8. The method of claim 7, wherein mixing the substance through the sample comprises mixing with a dynamic mixer of a high performance liquid chromatography system.

9. The method of claim 7, further comprising forming the sample with a mixture of oil, water, and salt by establishing a brine composition to recover the oil from a formation rock sample.

10. The method of claim 7, wherein using an optical technique to determine the quantity of oil in the sample comprises using a spectrophotometer.

11. The method of claim 7, wherein adding the substance further comprises adding a fluid mixture to an oil and brine, two-phase stream of the sample to create the optically clear mixture as a single-phase mixture.

12. The method of claim 7, wherein adding the substance further comprises adding an anionic surfactant.

13. A system for quantifying oil in a sample, comprising:
a mixing system to establish a brine composition;
a column in which oil is released from a formation sample upon introduction of the brine composition to create an oil, water, and salt sample;
a solubilizing mixing system in which a substance is introduced into the oil, water, and salt sample to create a single-phase mixture, wherein the substance comprises sodium bis(2-ethylhexyl)sulfosuccinate (AOT), isopropanol (IPA), and ethylenediaminetetraacetic acid-sodium salt (EDTA-4Na); and
a detection and analysis system for employing an optical technique to determine the quantity of oil in the oil, water, and salt sample.

14. The system of claim 13, wherein the detection and analysis system comprises a spectrophotometer.

* * * * *